(12) United States Patent
Klatz et al.

(10) Patent No.: US 6,277,143 B1
(45) Date of Patent: Aug. 21, 2001

(54) BRAIN COOLING APPARATUS AND METHOD FOR COOLING THE BRAIN

(75) Inventors: Ronald M. Klatz; Robert M. Goldman, both of Chicago, IL (US)

(73) Assignee: Life Science Holdings, Inc., Chicago, IL (US)

( * ) Notice: Subject to any disclaimer, the term of this patent is extended or adjusted under 35 U.S.C. 154(b) by 0 days.

(21) Appl. No.: 09/359,652

(22) Filed: Jul. 26, 1999

Related U.S. Application Data

(63) Continuation-in-part of application No. 08/910,156, filed on Aug. 13, 1997, now abandoned, which is a continuation-in-part of application No. 08/580,841, filed on Dec. 29, 1995, now abandoned, and a continuation-in-part of application No. 08/447,812, filed on May 23, 1995, now Pat. No. 5,913,885, which is a continuation of application No. 08/117,417, filed on Sep. 7, 1993, now abandoned, which is a continuation of application No. 07/704,038, filed on May 22, 1991, now Pat. No. 5,261,399.

(51) Int. Cl.⁷ .................................................. A61F 7/10
(52) U.S. Cl. .................... 607/104; 607/109; 607/110
(58) Field of Search .................................. 607/104, 108, 607/109, 110, 112, 114; 165/46; 383/901

(56) References Cited

U.S. PATENT DOCUMENTS

| | | |
|---|---|---|
| 2,521,780 | 9/1950 | Dodd . |
| 3,463,161 | 8/1969 | Andrassy . |
| 3,606,890 | 9/1971 | Gilbert . |
| 3,685,176 | 8/1972 | Rudy . |
| 3,871,381 * | 3/1975 | Roslonski ........................ 607/104 |
| 3,908,655 | 9/1975 | Lund . |
| 4,138,743 | 2/1979 | Elkins et al. . |
| 4,382,446 | 5/1983 | Truelock et al. . |
| 4,552,149 | 11/1985 | Tatsuki . |
| 4,572,188 | 2/1986 | Augustine et al. . |
| 4,691,762 | 9/1987 | Elkins et al. . |
| 4,750,493 | 6/1988 | Brader . |

(List continued on next page.)

FOREIGN PATENT DOCUMENTS

| | | |
|---|---|---|
| 30 39 468 | 5/1982 | (DE) . |
| 8607793 | 1/1987 | (DE) . |
| 0 449 299 A1 | 10/1991 | (EP) . |
| 2130489 | 6/1984 | (GB) . |
| 9000752 | 10/1991 | (NL) . |
| 446015 | 11/1974 | (SU) . |
| 454907 | 7/1975 | (SU) . |
| 652942 | 3/1979 | (SU) . |
| 904695 | 2/1982 | (SU) . |
| 1138152 | 2/1985 | (SU) . |
| 82/04184 | 12/1982 | (WO) . |
| 89/09583 | 10/1989 | (WO) . |

OTHER PUBLICATIONS

Talan, Jamie, "Brain Research: A Chilling Effect," *Newsday*, Apr. 14, 1992, p. 6.

*Primary Examiner*—Linda C. M. Dvorak
*Assistant Examiner*—R. Kearney
(74) *Attorney, Agent, or Firm*—Oliff & Berridge, PLC

(57) ABSTRACT

An apparatus and corresponding method are provided for treating or preventing at least one of brain, brain-stem and associated nervous tissue injuries in a mammal suffering from decreased or compromised blood flow to the brain. The apparatus includes a helmet configured to rest unsupported on the head of a mammal. The helmet includes outer and inner shells with at least one cavity intermediate the outer and inner shells for holding a coolant fluid within the at least one cavity, and a coolant source in communication with the helmet, the coolant source instantaneously providing a coolant fluid chilled to a temperature sufficient to slow the metabolism of the brain. When the coolant source is activated, the helmet becomes instantly chilled rapidly cooling the brain to a temperature sufficient to slow the metabolism of the brain a sufficient amount so that the mammal remains neurologically intact while efforts are made to restore regular blood flow to the brain of the mammal.

37 Claims, 12 Drawing Sheets

U.S. PATENT DOCUMENTS

| | | |
|---|---|---|
| 4,753,242 | 6/1988 | Saggers . |
| 4,765,338 | 8/1988 | Turner et al. . |
| 4,869,250 | 9/1989 | Bitterly . |
| 4,920,963 | 5/1990 | Brader . |
| 5,050,596 * | 9/1991 | Walasek et al. ............... 607/111 |
| 5,163,425 | 11/1992 | Nambu-et al. . |
| 5,184,612 | 2/1993 | Augustine . |
| 5,261,399 | 11/1993 | Klatz et al. . |
| 5,300,102 | 4/1994 | Augustine et al. . |
| 5,324,320 | 6/1994 | Augustine et al. . |
| 5,336,250 | 8/1994 | Augustine . |
| 5,350,417 | 9/1994 | Augustine . |
| 5,383,918 | 1/1995 | Panetta . |
| 5,486,207 | 1/1996 | Mahawili . |
| 5,539,934 | 7/1996 | Ponder . |
| 5,658,324 | 8/1997 | Bailey, Sr. et al. . |
| 5,683,438 | 11/1997 | Grahn . |
| 5,692,238 | 12/1997 | Watson, Jr. . |
| 5,735,890 | 4/1998 | Kappel et al. . |
| 5,755,756 | 5/1998 | Freedman, Jr. et al. . |
| 5,792,213 | 8/1998 | Bowen . |
| 5,871,526 | 2/1999 | Gibbs et al. . |

\* cited by examiner

BRAIN COOLING APPARATUS AND METHOD FOR COOLING THE BRAIN

This application is a continuation in part of U.S. patent application Ser. No. 08/910,156, filed on Aug. 13, 1997 now abandoned, which is a continuation in part of U.S. patent application Ser. No. 08/580,841 now abandoned, filed on Dec. 29, 1995, and of U.S. patent application Ser. No. 08/447,812 filed May 23, 1995, U.S. Pat. No. 5,913,885 which is a continuation of U.S. patent application Ser. No. 08/117,417 filed Sep. 7, 1993, now abandoned, which is a continuation of U.S. patent application Ser. No. 07/704,038 filed May 22, 1991, now U.S. Pat. No. 5,261,399.

BACKGROUND OF THE INVENTION

1. Field of Invention

The invention relates generally to treating ischemic and anoxic brain injuries. More particularly, the invention provides an apparatus and method for cooling of the brain and maintaining it at a temperature below normal body temperature during trauma or other periods of decreased or compromised blood flow due to, for example, stroke. With the invention, the brain and associated neurologic tissues survive the anoxic or ischemic trauma intact. The victim recovers with increased chances of survival and less chance of pennanent brain damage.

2. Description of Related Art

When an ischemic or anoxic injury occurs, the brain is deprived of freshly oxygenated blood. For example, this situation typically occurs during cardiac arrest, respiratory arrest, stroke and other cerebrovascular trauma, suffocation, drowning, strangulation, electrocution, toxic poisoning (carbon monoxide, cyanide, etc.), metabolic insults or other similar trauma. Without a steady supply of freshly oxygenated blood, the brain ceases to function and after resuscitation, most patients will suffer some damage to the brain and associated neurologic tissues.

For example, among cardiac arrest victims overall less than 10% survive neurologically intact and without significant brain damage. The other approximately 90% either die or sustain some neurologic injury from ischemia (i.e., lack of blood flow to the brain), or anoxia (i.e., lack of oxygen to the brain). Such frequency of neurologic injury occurs because after a cardiac arrest, basic cardiopulmonary resuscitation and advanced life support techniques, such as CPR, closed heart cardiac chest massage, and electroshock treatments, typically require fifteen to twenty minutes to regain circulation from a failed heart. Reversible neurologic damage begins as early as four minutes and irreversible neurologic damage begins as early as six minutes after circulation stops. To combat this potential neurologic injury, initial resuscitation efforts need to be directed toward reviving the brain in addition to resuscitating the heart.

As indicated above, anoxic and ischemic brain injuries from cardiac arrest, stroke or the like result in damage to the brain and associated neurologic tissues after about four minutes. In contrast, the heart can survive intact up to four hours after cardiac arrest, stroke or the like. The short viability of brain tissue upon deprivation of oxygenated blood is a result of the requirement of high amounts of nutrients for tissue maintenance. Brain tissue uses almost all of the nutrients supplied by the circulating blood for maintenance and stores only a small amount of nutrients. Absent blood flow to the brain, the small amount of stored nutrients is rapidly exhausted. Once exhausted, brain oxygen content is rapidly depleted. This oxygen depletion is traumatic and causes a series of reactions in the oxygen starved brain tissue cells. These reactions are believed to produce free radical ions, primarily consisting of the superoxide radical $O_2{-}^-$. These free radicals complex with proteins in the brain and associated neurologic tissues, altering respiration, energy transfer and other vital cellular functions, and irreversibly damage these tissues.

Efforts should be directed toward resuscitating the brain to attempt to extend the period of time the brain can function without oxygen while the patient remains neurologically intact. The medical literature is replete with examples of humans surviving extended periods of time (greater than 5 minutes) without oxygen being delivered to the brain.

Hypothermic therapy is one method of keeping the brain alive absent oxygen. It involves cooling the brain to a temperature where its metabolic activity is decreased. When the brain's metabolic activity is decreased, it uses much less oxygen and stored nutrients are exhausted slowly, while production of irreversibly damaging $O_2{-}^-$ free radicals is slowed and almost completely ceased. Thus, upon resuscitating the body from trauma, the patient emerges neurologically intact. For example, children revived after hours of submersion in very cold water have fully recovered with little if any neurologic damage.

Cooling for hypothermic therapy is presently achieved by cold room technology involving a heat exchanger in a heart-lung bypass. The surgery involved with the cold room technology takes place in a room the size of a meat locker or large commercial freezer. Cooling is also achieved by traditional devices such as natural or synthetic ice packs. Both of these devices and methods have several drawbacks.

A major drawback with the cold room technology is that it is invasive and quite expensive. It involves a team of highly trained, skilled medical personnel to operate and supervise a standard heart-lung bypass machine. This technology is not portable as it is restricted to a surgical operating room setting. Also, cooling is progressive, not instantaneous. Natural or synthetic ice packs, although portable and non-invasive, are disadvantageous because they are messy and do not rapidly achieve the low temperatures required to hypothermically shock the brain. Additionally, ice packs are ineffective in extremely hot environments such as deserts because they melt rapidly.

Previous inventions, such as those described in U.S. Patents Nos. 5,149,321 to Klatz et al. ('321), U.S. Pat. No. 5,234,405 to Klatz et al. ('405) and U.S. Pat. No. 5,261,399 to Klatz et al. ('399), address the need to direct resuscitation efforts toward the brain, such that the victim can survive ischemic or anoxic trauma neurologically intact. Specifically, the '321 and '405 patents discuss devices and methods for resuscitating the brain such that its metabolism is slowed in order that the victim survive these metabolic insults neurologically intact. The '399 patent discloses a device and method for externally cooling the brain and associated tissues.

Along with brain cooling, it can be advantageous to cool internal organs in the body such that their metabolism is slowed in order that they survive these metabolic insults fully intact. Typical current methods for cooling organs include ice packs or large scale machinery, such as that disclosed in U.S.S.R. Patent No. 1138152A ('152). However, these methods and devices both have drawbacks. Ice packs are typically small in area, and when applied to a person, do not provide the rapid cooling necessary to slow the metabolism of internal organs. The device disclosed in the U.S.S.R. '152 patent exhibits the drawback of providing cryogenic cooling that is too extreme for organ resuscitation during metabolic insults. This device is not suited for field use, as it is a large structure restricted to clinical facilities capable of handling dangerous fluids such as liquid nitrogen. Moreover, it must be used by a skilled surgical team and maintained by skilled technicians.

OBJECTS OF THE INVENTION

It is an object of this invention to non-invasively treat ischemic and anoxic brain injuries promptly upon cardiac arrest, stroke or the like whereby resuscitation efforts are applied in time for a patient to survive neurologically intact. By directing resuscitation efforts to treat the brain promptly, the invention allows medical personnel substantial additional time (beyond the critical four minute window) to regain the failed heart's circulation without the patient suffering permanent neurologic damage.

It is also an object of this invention to provide a method for treating anoxic or ischemic injuries to the brain whereby the patient survives neurologically intact.

It is also an object of the invention to provide a method of treating ischemic and anoxic brain injuries so as to inhibit free radical chemical species from complexing with proteins in the brain and neurologic tissue to avoid permanent irreversible damage.

It is also an object of the invention to non-invasively treat ischemic and anoxic brain injuries.

It is a further object of the invention to provide an apparatus which can substantially instantaneously cool the brain to a temperature where brain metabolism is slowed.

It is a further object of the invention to provide a portable apparatus for noninvasively treating anoxic and ischemic brain injuries which can substantially instantaneously cool the brain and associated neurologic tissue.

It is a further object of the invention to provide an apparatus for treating the aforementioned injuries by instantaneously cooling the brain, associated neurologic tissues and the upper spinal column.

It is a further an object of the invention to provide an apparatus for treating the aforementioned injuries, which is suited for field as well as clinical use and that can be operated by a single person with minimal medical training and experience.

It is a still further object to provide apparatus for cooling the brain which has very few parts, and is economical to manufacture and easy to use.

Other objects and advantages of the invention will be apparent to those skilled in the art from the following description and the appended claims.

SUMMARY OF THE INVENTION

The invention focuses on initial resuscitation efforts toward resuscitating the brain, due to its short viability, rather than the heart. The invention includes a noninvasive method which inhibits neurologic damage and resulting ischemic and anoxic injury on decreased or compromised blood flow, e.g., due to cardiac arrest, stroke or the like. The method includes placing and adjusting a scalp-enveloping helmet provided with means therein for circulation of a coolant fluid and circulating within said helmet a coolant fluid so as to lower the temperature of the patient's brain. In embodiments, substantially simultaneously with the circulation of coolant fluid through the scalp-enveloping helmet a neck supporting back plate shaped to correspond with the natural curvature of the neck is put in place to support the patient's neck in an upward position. The coolant fluid may also circulate through the back plate.

The invention also provides novel apparatus for alleviating ischemic and anoxic brain injuries in a mammal suffering from cardiac arrest, stroke or the like. The apparatus of the invention provides a helmet-like scalp-enveloping element provided with means therein for circulation of a coolant fluid. The scalp-enveloping element may be provided with inlet means for receiving a coolant fluid from a coolant fluid source to which it is operatively connected. The coolant source may include a portable coolant tank containing compressed liquid, the portable coolant tank being in fluid communication with at least one cavity of the scalp-enveloping element via a tube. Outlets may be provided in the scalp-enveloping element to permit the discharge therefrom of coolant fluid after circulation through the element.

Further, the coolant source may be a charging mechanism disposed on an outer surface of the outer shell of the scalp-enveloping element which upon activation produces the chilled coolant fluid. Alternatively, the coolant source may be disposed within the at least one cavity. For example, it may include a packet containing chemicals which are activated upon mixing to produce the chilled coolant fluid. Also, the coolant source may be a chemical disposed within the at least one cavity which produces the chilled coolant fluid when activated, e.g., by water.

Embodiments of the apparatus also include a neck supporting back plate shaped to correspond with the natural curvature of the patient's neck. The neck supporting back plate may also be provided with means therein to permit passage of coolant fluid therethrough. Means may be provided to allow for fluid communication between the scalp-enveloping element and the neck supporting back plate so that coolant fluid can be circulated through both pieces in series.

Inner and outer shells of the scalp-enveloping element may be formed of a soft, flexible material. Further, padding may be disposed on a surface of the inner shell of the scalp-enveloping element, the padding being of a material which allows the chill to quickly reach the brain. Additionally, the apparatus may be configured to be disposable and may include a flexible adjusting mechanism for maintaining the scalp-enveloping element on the head of a mammal.

Additionally, the scalp-enveloping element may include at least one coolant distributing system and may further include an inflatable bladder for pressing the scalp-enveloping element against the head of a mammal, whereby the head of the mammal is rapidly cooled.

Further, the scalp-enveloping element may include at least one temperature sensor for sensing a temperature of the chilled coolant fluid within the scalp-enveloping element.

Moreover, a layer of gel may be disposed on an inner surface of the inner shell and portions of the scalp-enveloping element may extend to cover the forehead and cheeks of the head of a mammal and a portion that extends to cover the eyes of a mammal.

BRIEF DESCRIPTION OF THE DRAWINGS

The invention will be described with reference to the accompanying drawings, wherein like reference numerals identify corresponding or like components.

In the drawings.

DETAILED DESCRIPTION OF PREFERRED EMBODIMENTS

Figure 1:
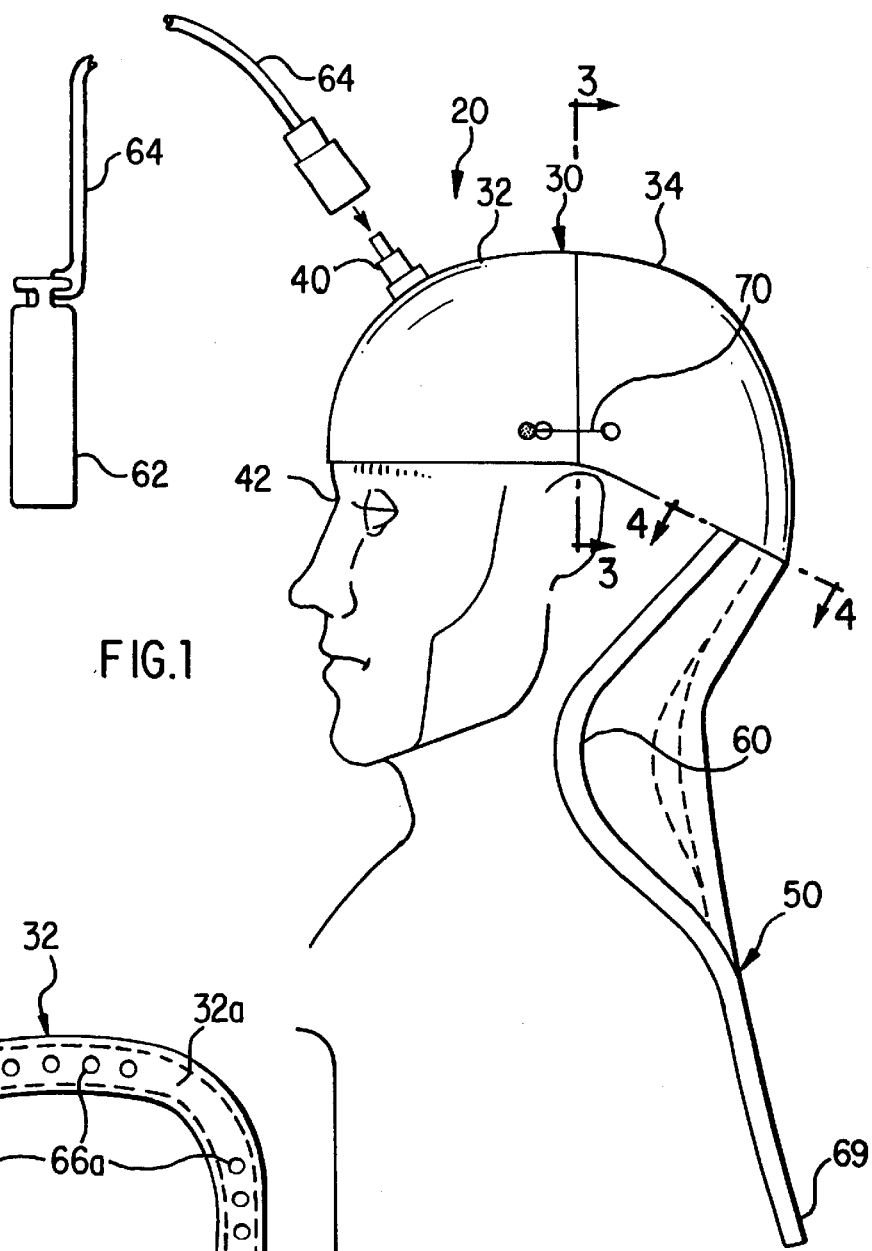
FIG. 1 is a side view of a brain cooling apparatus according to the invention.

Referring to FIG. 1, this embodiment of the brain cooling device 20 includes an adjustable multiple piece scalp-enveloping element or helmet 30, a back plate 50 and a coolant source 62. All of these components are designed to cooperatingly fit together. These components are lightweight and portable. They can be easily and quickly assembled together immediately prior to use at the site of the trauma. Detachment is also simple and quick.

Figure 2:
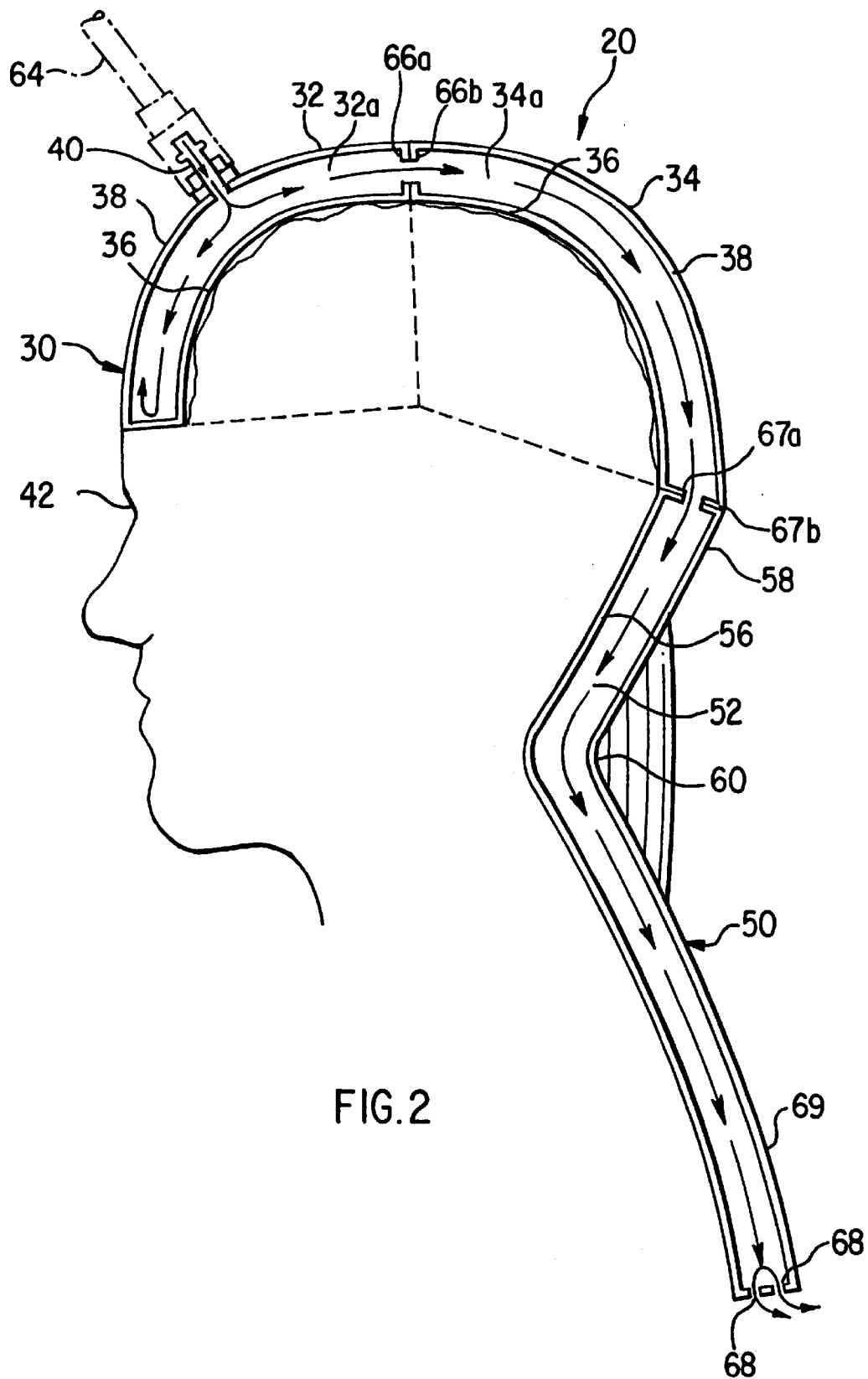
FIG. 2 is a cross-sectional view of a brain cooling apparatus according to the invention.

The scalp-enveloping element or helmet 30 is of a universal size to insure conformity to all head sizes. While a two piece constriction is preferred, one-piece or multiple piece helmets are also possible. Each helmet piece 32, 34 has a hollow cavity 32a, 34a between the inner shell 36 and the outer shell 38 (FIG. 2). The helmet 30 includes flexible adjustment mechanisms 70 on both sides with cooperating coupling elements on each piece (or segment with one-piece helmets) enabling conformity to all head sizes. The front piece 32 of the helmet 30 has at least one outwardly extending nipple 40 to receive coolant, which enters this front piece 32 into the hollow cavity 32a, whereby coolant circulates throughout all of the hollow cavities 32a, 34a, 52 (see FIG. 2) in each helmet piece 32, 34 and in the back plate 50, cooling the inner shell 36 (FIG. 2) of the helmet 30. The chill penetrates the inner shell 36 (FIG. 2) to contact the patient's head 42 at a temperature sufficiently low to quickly slow the brain's metabolism and inhibit potential neurologic damage.

The back plate 50 is preferably a one piece unit, although multiple piece construction is also permissible. Like the helmet pieces 32, 34, the back plate 50 has a large hollow cavity 52 between the inner shell 56 and the outer shell 58 (FIG. 2). Back plate 50 supports the neck and permits additional cooling of the brain stem and upper spinal column. The back plate 50 can be maintained in fluid connection with the helmet 30 by body weight alone in an abutment relationship. However, fastening means such as buckles, straps, tape, snaps, rods, snap-together molding or other suitable fasteners can be used. Preferably, back plate 50 is saddle shaped at its upper portion 60 to accommodate and exaggerate the natural curvature of the neck, hyperextending it, while positioning it upwards. In this position, the carotid arteries or other large neck vessels are exposed and easily accessible for catherization involved with other resuscitation methods.

The coolant source 62 is preferably a compressed liquid such as carbon dioxide, which upon decompression becomes a cold gas. Prior to activation, these cold compressed liquids are preferably stored in portable containers such as tanks. Other suitable compressed liquids include freon or nitrogen. Alternatively, very cold liquids such as supercooled water, self freezing gel, packed liquid, ice water, or other such chemicals may be passed into the helmet through a tube 64 operatively connected to the nipple 40.

Figure 9:
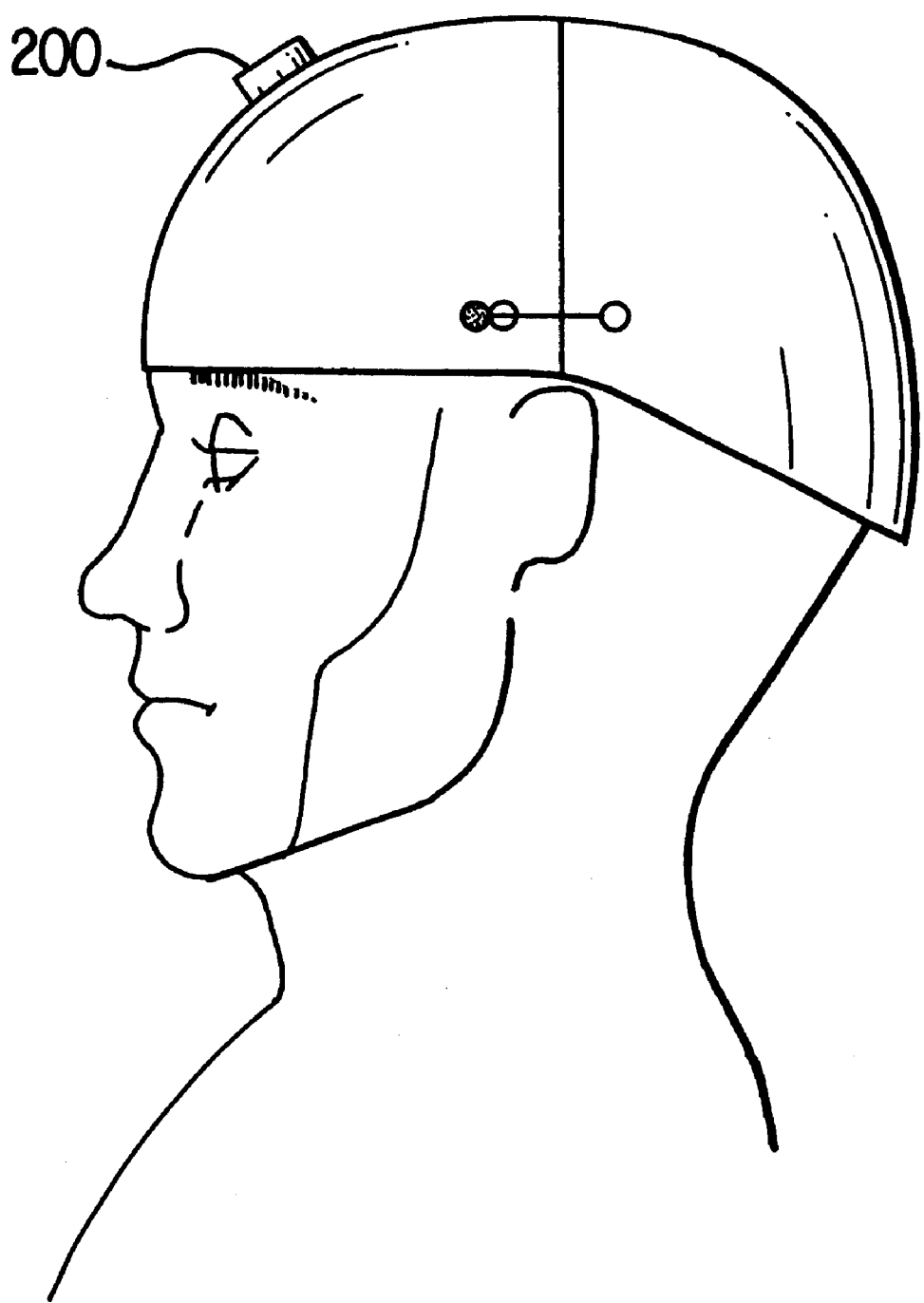
FIG. 9 is a side view of a brain cooling apparatus of the invention where the coolant source is a charging mechanism.
Figure 10:
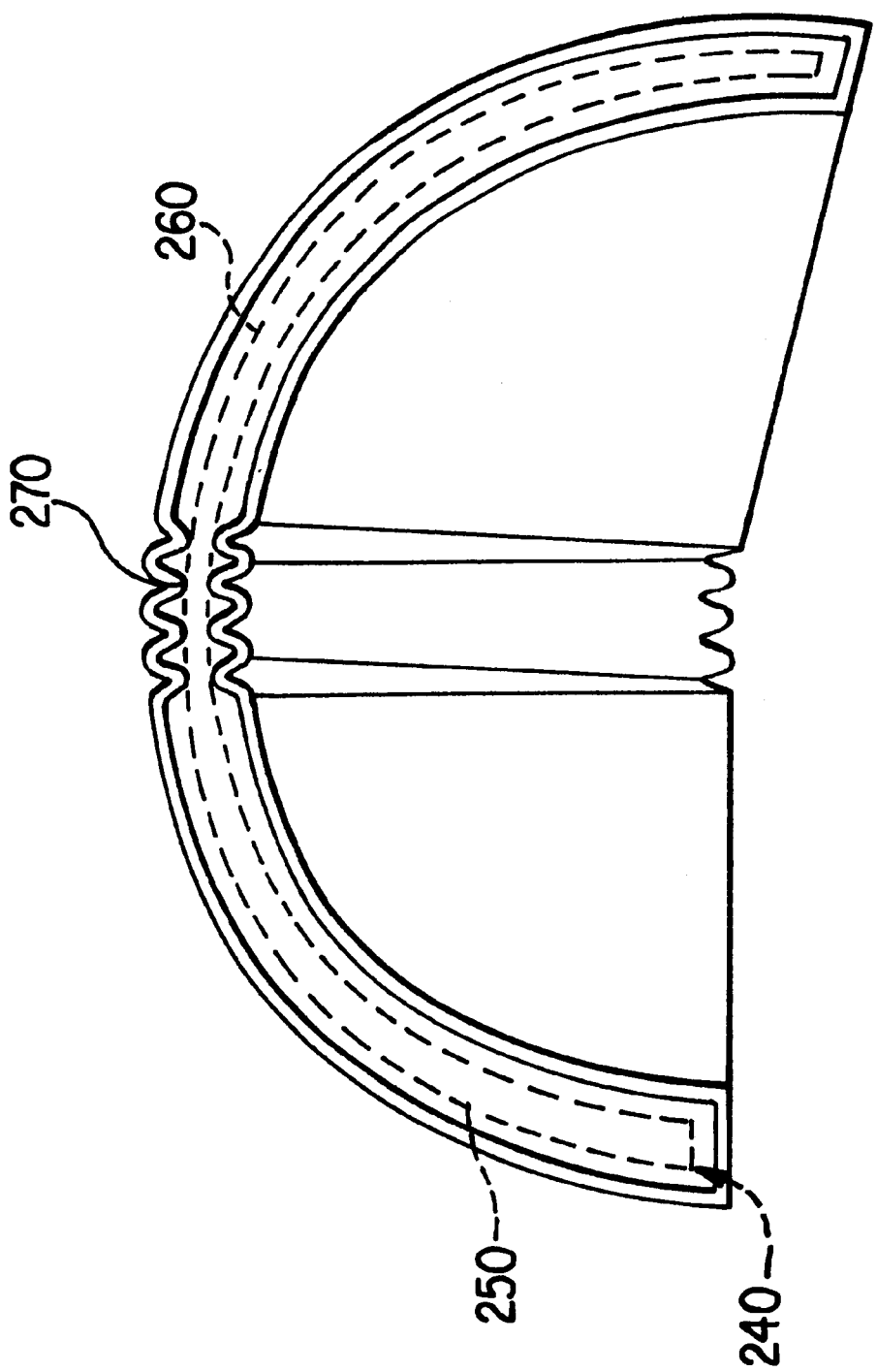
FIG. 10 is a cross-sectional view of a brain cooling apparatus according to the invention where the coolant source is a chemical pack.

An additional alternative coolant involves materials within the hollow cavities of the helmet, the back plate, or both, which chill upon activation when use is desired. For example, the helmet, back plate, or both could be prefilled with ammonium nitrate or equivalent thereof, which reacts endothermically when activated by water to chill these pieces. Alternatively, they could be provided with a charging mechanism 200 filled with compressed carbon dioxide or another compressed gas disposed on the outer surface of the helmet to provide instant cooling, as shown in FIG. 9. FIG. 10 shows an example of a chemical packet 240 disposed within the inner cavity which activates when the membrane 270 between two separate chemical compartments 250, 260 is broken to mix the two chemicals, providing instant cooling. However, such a helmet would not be reusable unless configured so that the chemical packet 240 can be replaced.

FIG. 2 is a cross-sectional view of the helmet and back plate pieces of the first embodiment of the invention shown in FIG. 1. This view shows the coolant's circulation between these components in detail. A specific circulation path is shown by arrows.

Coolant fluid, consisting of gas and/or very cold liquid, moves by expansion from the coolant source 62 through a tube 64 to the nipple 40 on the front piece 32 of the helmet 30. This nipple 40 is preferably located on the front piece 32 of the helmet 30 since its angular orientation away from the body provides easy tube accessibility. However, single or multiple nipples can be placed on any of the helmet 32, 34 or back plate 50. Coolant then enters the hollow cavity 32a in the front piece 32 of the helmet 30, and circulates throughout the hollow cavities 34a, 52 of the rear helmet 34 and back plate 50 pieces.

Figure 3:
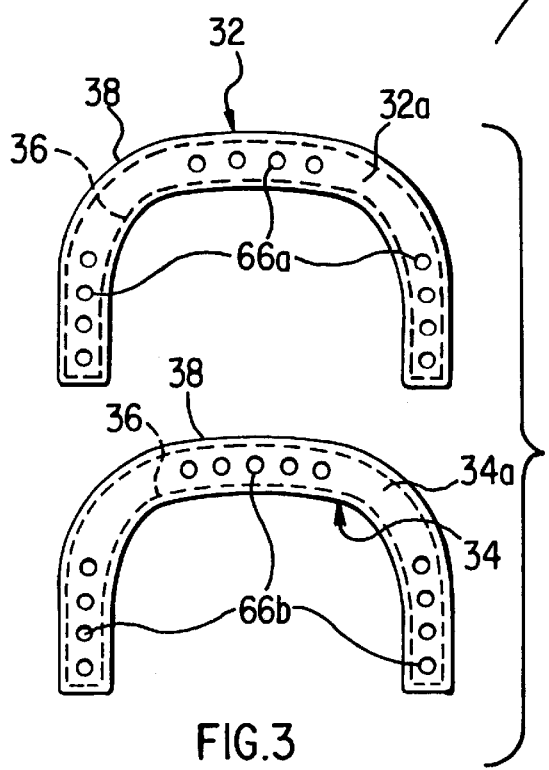
FIG. 3 is a cross-sectional view of the interface of the front and rear helmet pieces taken along line 3—3 of FIG. 1.
Figure 4:
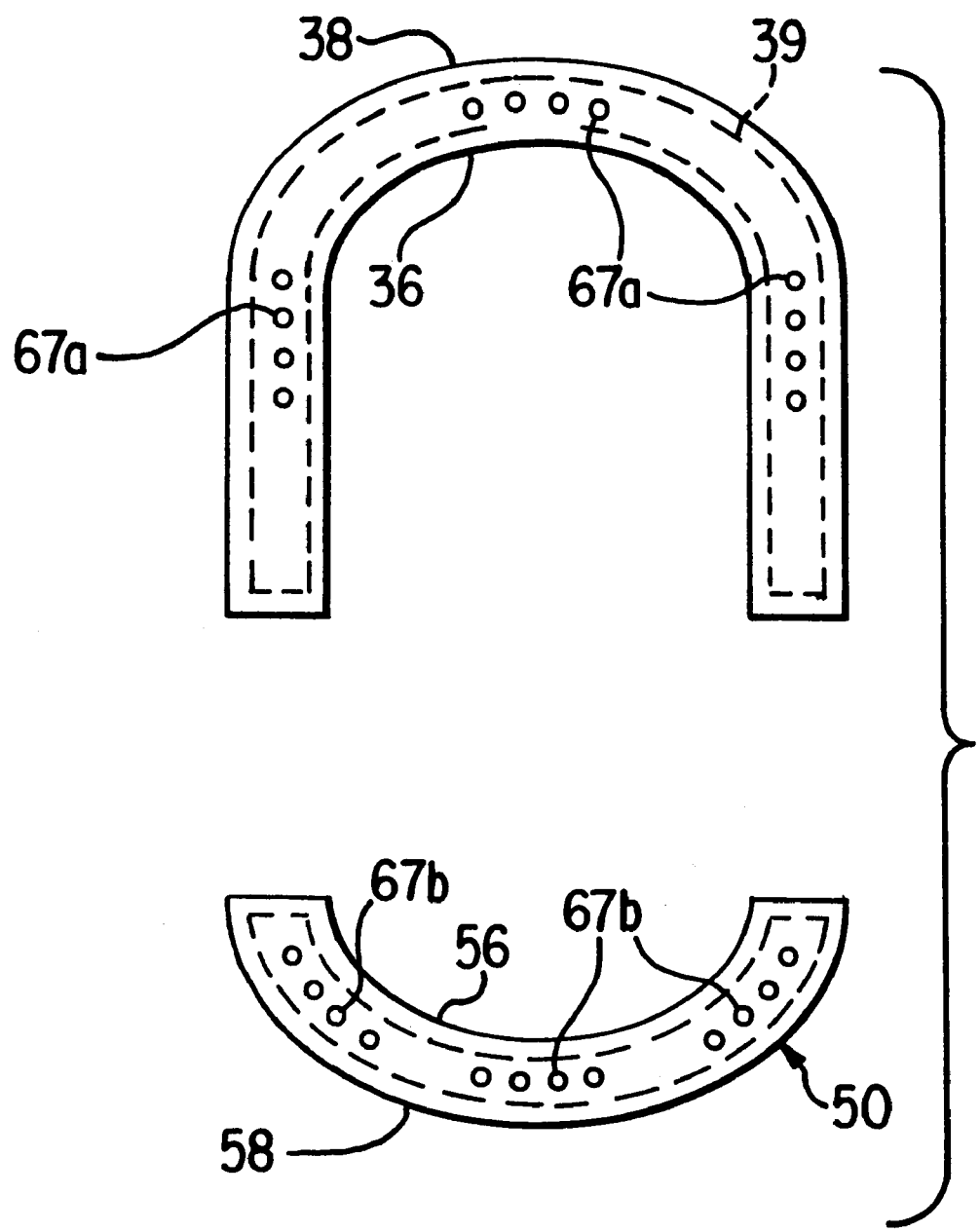
FIG. 4 is a cross-sectional view of the interface between the rear helmet and back plate pieces taken along line 4—4 of FIG. 1.

Coolant may circulate throughout the helmet 32, 34 and back plate 50 through cooperatively aligned circulation ports 66a, 66b, 67a, 67b located on the respective ends of each helmet 32, 34 and back plate 50 piece. FIG. 3 shows these cooperatingly aligned circulation ports 66a, 66b at the interface of the front 32 and rear 34 helmet pieces respectively, while FIG. 4 shows these cooperatingly aligned circulation ports 67a, 67b at the interface of the rear helmet 34 and the back plate 50 pieces. The outer and inner shells between the hollow cavities in these helmet and back plate pieces is shown in phantom. While the illustrated port arrangement is preferred, any alternate arrangement is also permissible provided this arrangement permits chilled fluid to circulate throughout the helmet 30 and the back plate 50.

Coolant exits the system through exhaust ports 68, in the lower portion 69 of the back plate 50. Additional exhaust ports may also be located on the helmet pieces to accommodate possible increased pressure. These exhaust ports would aid in eliminating any potential pressure build up in the hollow chambers which might damage the helmet 32, 34 or the back plate 50 pieces.

Preferred helmet 32, 34 and back plate 50 pieces may be made of a polymeric material such as blow molded plastics, nylon, fiberglass or rubber; metal or the like. This material is able to withstand contraction from rapid cooling and subsequent expansion upon warming without cracking. The inner helmet shell 36 is thin enough to conduct the chill from the hollow cavities 32a, 34a, 52 to the brain at a temperature sufficiently low to quickly slow brain metabolism, and inhibit potential neurologic damage. The inner helmet shell 36 is also thick and tough enough to support the patient's head 42 without deforming when the helmet is adjusted and placed on the patient's head 42. However, soft shell or cloth-like helmets or helmet segments are also permissible provided they have a hollow cavity which can sufficiently receive and circulate coolant fluid.

Padding (not shown) may also be included on the inner helmet shell 36 and back plate inner shell 56 for additional comfort. However, this padding should be of a material such as sponge or the like which allows the chill to quickly reach the brain.

Figure 5A:
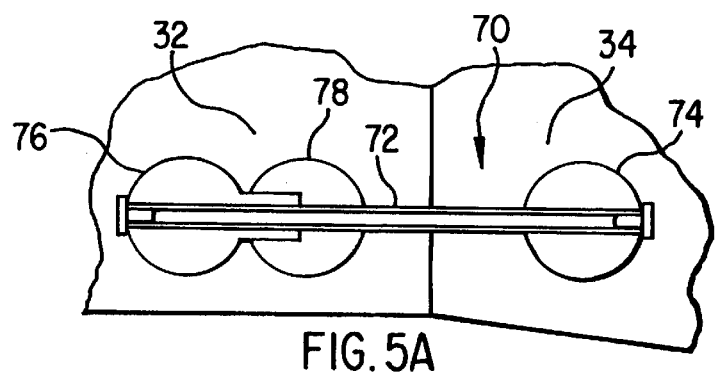
FIGS. 5A and 5B are side and top partial sectional views of the helmet adjustment mechanism.
Figure 5B:
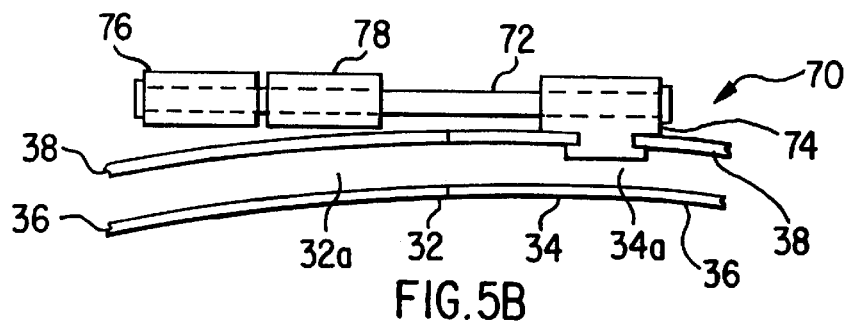

FIGS. 5A and 5B show adjustment and attachment mechanisms 70 for the helmet pieces 32, 34. Exemplary elements include flexible tension straps 72 permanently mounted in a first anchor 74, affixed to the outer helmet shell 38 and mounted in freely moving latch handles 76. These flexible tension straps 72 are elastic enough to allow for adjustment to various head sizes, yet resilient enough to maintain the helmet's compression fit on the patient's head 42. A first anchor 74 is permanently affixed to the outer shell 38 of the rear helmet piece 34 while the latch handle 76 is free and mounts at a point forward of a second anchor 78. This second anchor 78 is permanently affixed to the outer shell 38 on the front piece 32 of the helmet 30, and accommodates the flexible tension strap 72 through its center as the latch handle 76 abuts the second anchor 78 upon securement. While this arrangement between the latch handle 76 and anchors 74, 78 is preferred, the opposite arrangement of a permanently affixed anchor to the front helmet piece, including the permanently mounted flexible tension strap and a permanently affixed anchor to the rear helmet piece, is also permissible. Alternately, the helmet pieces can be held together by straps, buckles, tape, manual compression, or other similar attachment devices.

While this first embodiment is preferably a three piece unit (two helmet pieces and a back plate piece) the brain cooling device is also effective with only a front helmet piece which is activated with coolant and is manually pressed against the head. This is also true for the other helmet piece(s) and the back plate or pieces thereof, which can also function separately if equipped with nipples or other suitable means and provided with coolant sources.

This embodiment of the brain cooling device is relatively small. It is portable, can be fitted into a suitcase-like carrying case, and is suitable for field use, such as in ambulances, battlefields, athletic fields, aircraft, marine vehicles, spacecraft, emergency treatment facilities, and the like. It is lightweight and can be carried directly to the patient. In one example, the brain cooling device fits in a suitable carrying case and weighs approximately thirteen pounds or less.

Figure 6:
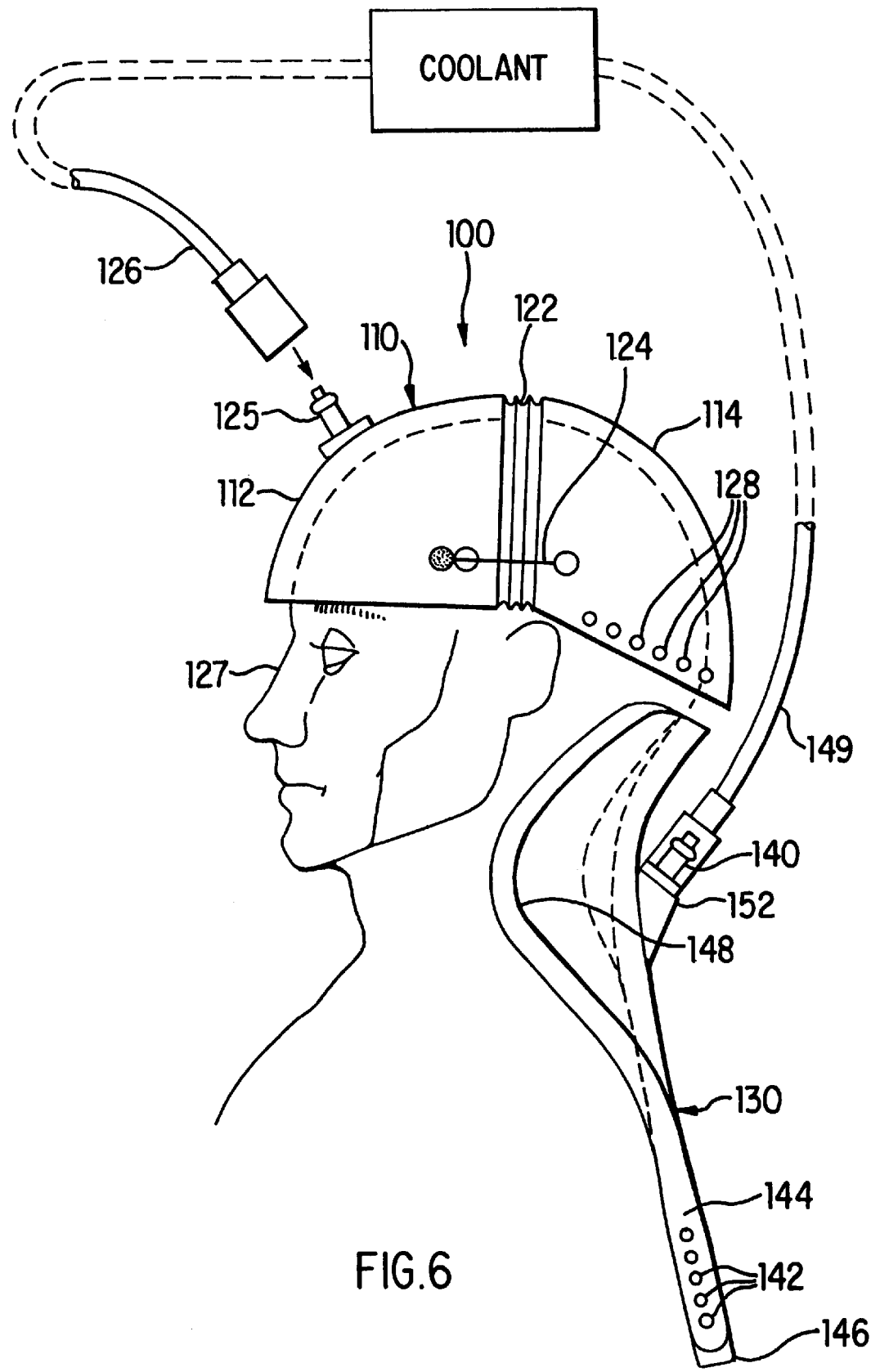
FIG. 6 is a side view of another embodiment of a brain cooling according to the invention.

FIG. 6 depicts a second embodiment of the brain cooling device 100. This embodiment is made of two pieces: a one piece helmet 110 with front and rear segments 112, 114 in combination with a back plate 130. Both the helmet 110 and the back plate 130 may be operatively connected to coolant sources (not shown). The coolant sources 112 employed with this embodiment are similar to those disclosed above in relation to the first embodiment. Like the first embodiment, these components are preferably lightweight and portable. They can be easily and quickly assembled together immediately prior to use at the site of the trauma. Detachment is simple and quick. Although these components are designed to operate as a unit, either the helmet 110 or the back plate 130 can be used separately should it be necessitated or desired.

Figure 7:
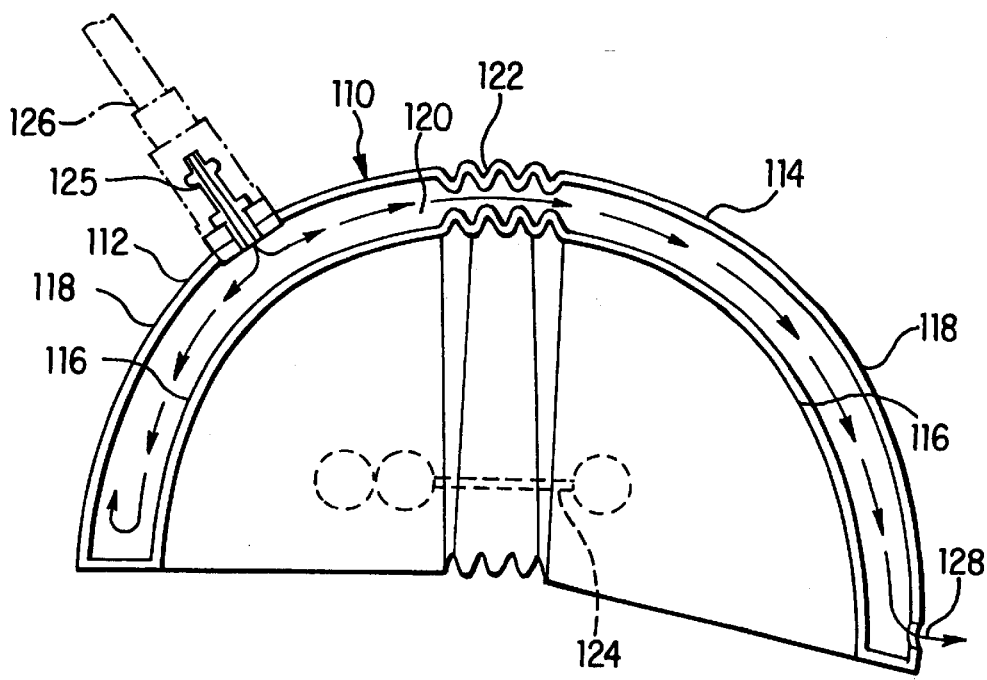
FIG. 7 is a cross-sectional view of the embodiment of the brain cooling apparatus shown in FIG. 6.

The preferred helmet 110 is of a universal size to insure conformity to all head sizes. The helmet has inner 116 and outer 118 shells with a cavity 120 therebetween (FIG. 7). The two helmet segments 112, 114 are separated by a side-to-side baffled connector 122. This baffled connector 122 is preferably of an elastomeric or other suitable flexible material with several folds on both shells. This baffled connector 122 allows the helmet 110 to be adjusted to various head sizes. While a side-to-side connection is preferred, a front to rear connection is also permissible. While baffled or folded connectors are preferred, other flexible, resilient, elastomeric connectors are also suitable. Also, while two helmet segments 112, 114 are preferred, additional segments are also permissible provided these segments are separated by baffled or other suitable connectors. Flexible adjustment mechanisms 124, preferably on both sides of the helmet 110, provide further adjustability. These adjustment mechanisms may be identical to those disclosed for the preferred embodiment as illustrated in FIG. 5.

The front helmet segment 112 has at least one outwardly extending nipple 125 to receive coolant from a tube 126. The nipple 125 in the front helmet segment 112 extends into the hollow cavity 120 for circulating coolant throughout the entire hollow cavity 120 (see FIG. 7), cooling the inner shell 116 of the helmet 110. The chill penetrates the inner shell 116 to contact the patient's head 127 at a temperature sufficiently low to quickly slow the brain's metabolism and inhibit potential neurologic damage. The helmet 110 also includes exhaust ports 128 at its lower end to allow coolant to leave the helmet 110 and equalize pressure, whereby the helmet 110 does not crack or sustain other damage.

Figure 8:
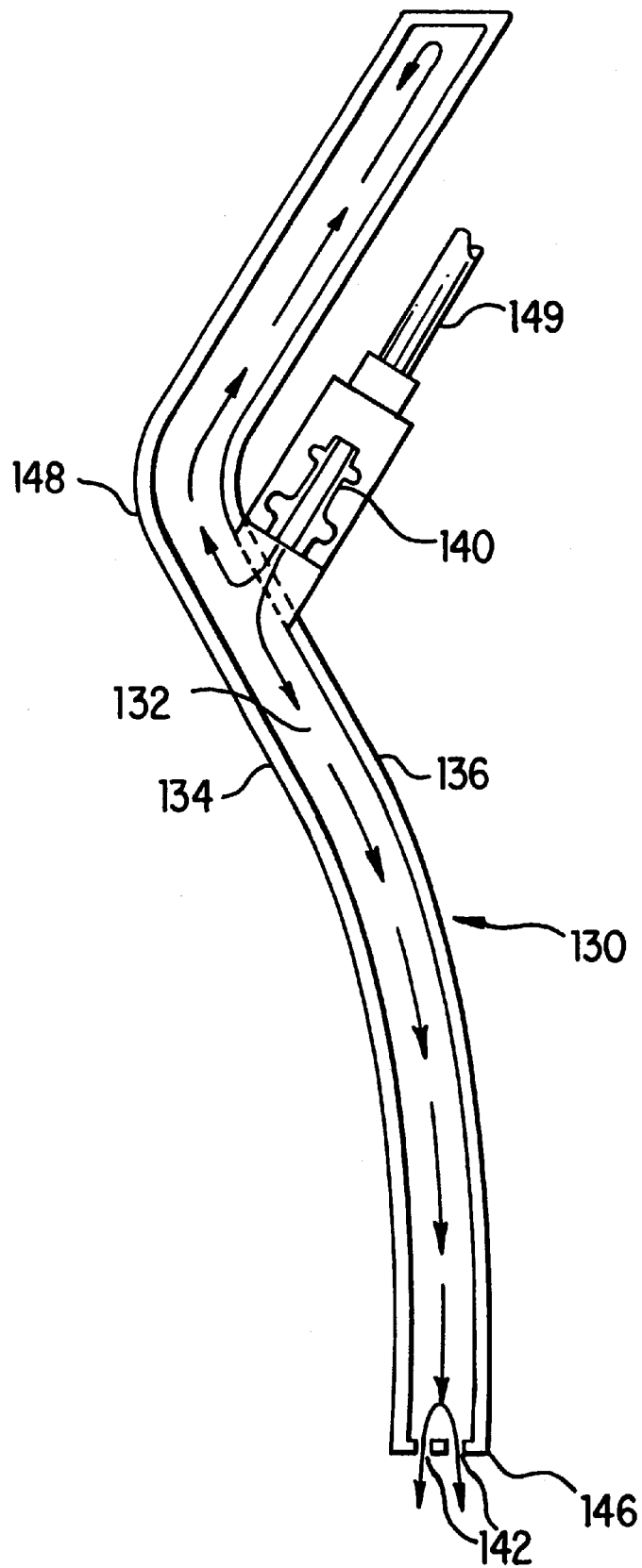
FIG. 8 is a cross-sectional view of the back plate of the embodiment of the brain cooling apparatus shown in FIG. 6.

The back plate 130 provides additional cooling for the brain stem and upper spinal column. It is preferably a one piece unit, although multiple piece construction is permissible. Like the helmet 110, the back plate 130 has a large hollow cavity 132 between the inner shell 134 and outer shell 136 (FIG. 8). The back plate 130 is separate from the helmet 110 during use. The back plate 130 includes a centrally positioned nipple 140 to receive coolant. Single or multiple nipples placed at other locations on this back plate or any pieces thereof are also permissible. The back plate 130 includes exhaust ports 142 along the perimeter 144 of the back plate's lower portion 146 to allow coolant to leave, equalizing pressure in the cavity 132 to prevent damage to the back plate 130, such as cracking. Additional or substitute exhaust ports can be placed anywhere on the back plate.

Like the preferred embodiment, this back plate 130 supports the neck. It has a saddle shaped upper portion 148 to accommodate and exaggerate the natural curvature of the neck, hyperextending it, while positioning it upwards. In this position, the carotid arteries or other large neck vessels are exposed and easily accessible for catherization involved with other resuscitation methods.

FIG. 7 is a cross-sectional view of a helmet of this second embodiment. This view shows the coolant's circulation between the helmet segments 112, 114 in detail. The specific circulation path is shown by arrows.

Coolant fluid, comprised of gas at a low temperature or very cold liquid, moves by expansion from the coolant source (not shown) through a tube 126 operatively connected to the nipple 125 on the front segment 112 of the helmet 110. This nipple 125 is preferably located on the front segment 112 of the helmet 110 since its angular orientation away from the body provides easy tube accessibility. However, single or multiple nipples can be placed on any of the helmet segments 112, 114. Coolant then enters the hollow cavity 120 in front helmet segment 112, and circulates through the baffled connector 122 to the rear helmet segment 114. Coolant exits the system through exhaust ports 128, preferably located on the lower portion of the rear helmet segment 114. Additional or substitute exhaust ports may also be located anywhere on any of the helmet segments to accommodate possible increased pressure.

FIG. 8 is a cross-sectional view of a back plate 130 of this second embodiment. This view shows the coolant's circulation within this back plate's hollow cavity 132 between the inner and outer shells 116, 118 in detail. The circulation path is shown by arrows.

Similar to the helmet 110, the coolant fluid, comprised of very cold gas or liquid, moves by expansion from the coolant source (not shown) through a tube 149 to the nipple 140 on the bottom side 152 of the back plate 130. This nipple 140 is preferably centrally located on the curved upper portion 148 to provide easy tube accessibility. Coolant then enters the hollow cavity 132 and circulates throughout the entire back plate 130. Coolant exits the back plate 130 through the exhaust ports 142, preferably located on the perimeter 144 of the lower portion 146. Additional or substitute exhaust ports may also be located anywhere on this back plate 130 to accommodate possible increased pressure.

Similar to the first preferred embodiment, the helmet 110 and back plate 130 of the embodiment may be made of a polymeric material such as blow molded plastics, nylon, fiberglass, or rubber; metal; or the like. This material is able to withstand contraction from rapid cooling and subsequent expansion upon warming without cracking. The inner helmet shell 116 is thin enough to conduct the chill from the hollow cavity 120 to the brain at a temperature sufficiently low to quickly slow brain metabolism and inhibit potential neurologic damage. The inner helmet shell 116 is also thick and tough enough to support the head without deforming when the helmet 110 is adjusted and placed on the patient's head 127. However, soft shell or cloth-like helmets are also permissible provided they have a hollow cavity which can sufficiently receive and circulate coolant fluid.

Padding (not shown) may also be included on the helmet 116 and back plate 134 inner shells for additional comfort. However, this padding should be of a material such as sponge or the like which allows the chill to quickly reach the brain.

While these two preferred embodiments described in detail herein are portable devices particularly suited for field use, they are also suited for stationary, clinical use. Should a clinical device be desired, these two portable embodiments could be made larger and modified accordingly for such use.

In operation, the brain cooling apparatus of the invention sufficiently chills the brain to slow its metabolism, allowing for continued resuscitation efforts. As previously stated, the invention comprises a method of treating anoxic and ischemic injuries suffered as a result of cardiac arrest, respiratory arrest, stroke or other cerebrovascular trauma, suffocation, drowning, electrocution, toxic poisoning (carbon monoxide, cyanide, etc.) metabolic insults or other similar trauma.

Specifically, operation of the apparatus involves merely placing the patient on the back plate (if a back plate is present), attaching the helmet pieces (if using a multiple piece helmet), adjusting the helmet on the patient's head, attaching the helmet to the back plate, attaching a tube from the nipple(s) to the coolant source(s) and activating the coolant source(s). This process is quite simple and can be performed at the trauma site by a person with minimal, if any, medical training.

Figure 11:
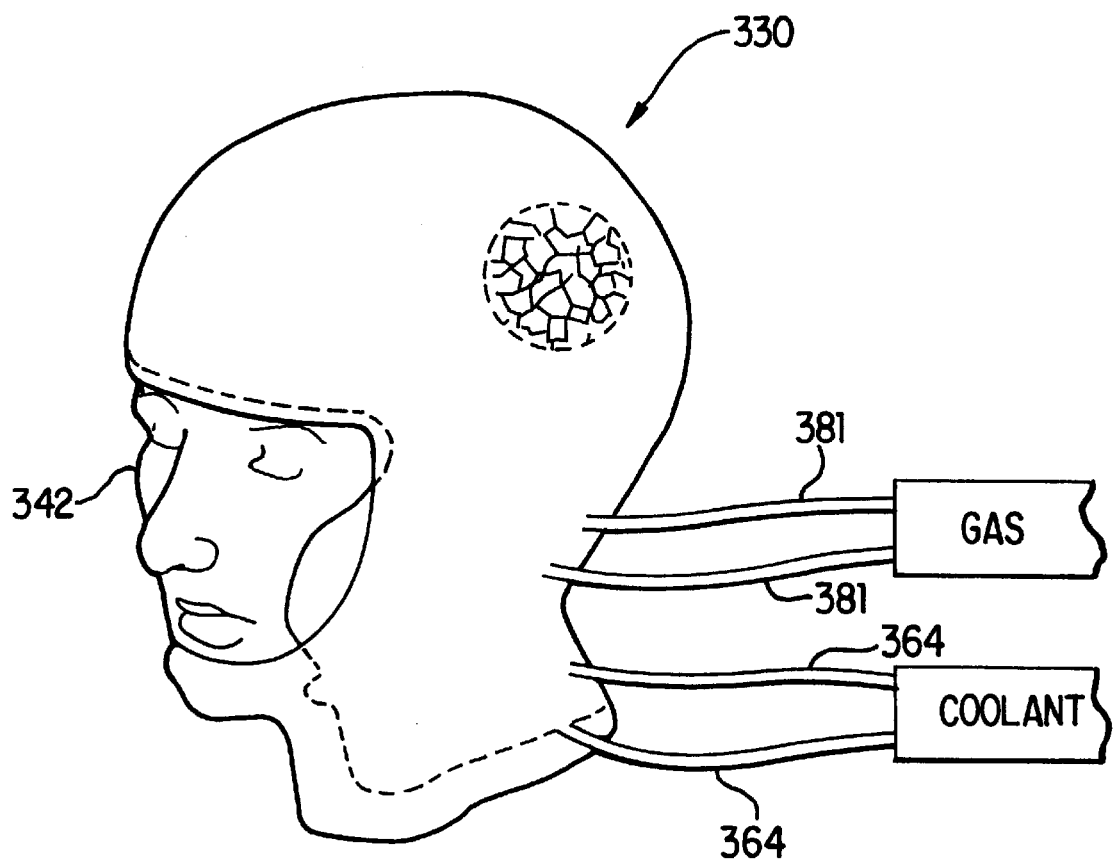
FIG. 11 is a perspective view of another embodiment of a brain cooling apparatus according to the invention.
Figure 12:
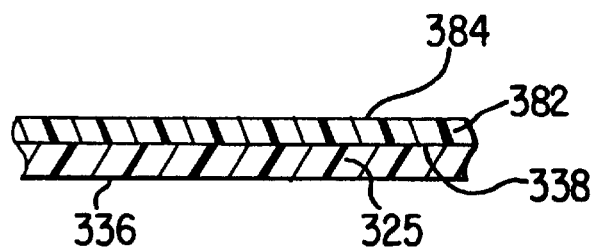
FIG. 12 is a side cross-sectional view of the brain cooling apparatus of FIG. 11.

FIG. 11 shows another embodiment of the brain cooling apparatus according to the invention. The brain cooling apparatus 330 includes an outer shell 338 connected to an inner shell 336 that when attached form a cavity 325 therebetween (see FIG. 12). The apparatus 330 is designed to move coolant fluid (liquid or gas) from a coolant source 362 and circulate it through cavity 325 to cool the head 342. Inflow and outflow lines 364, 364 for delivering and returning coolant fluid from and to the coolant source 362 are attached to outer shell 338.

Figure 12A:
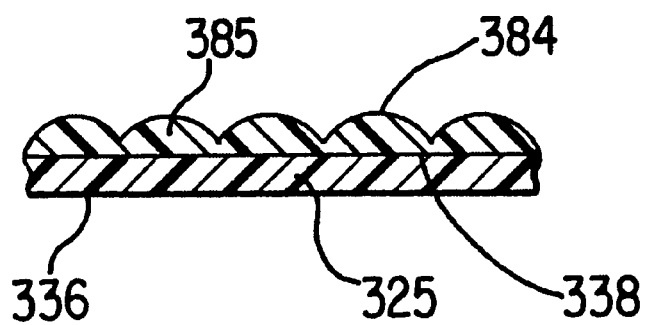
FIG. 12A is a side cross-sectional view of another embodiment of the brain cooling apparatus of FIG. 11.
Figure 12B:
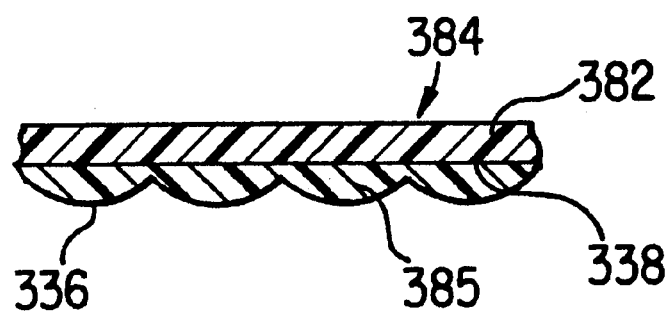
FIG. 12B is a side cross-sectional view of another embodiment of the brain cooling device of FIG. 11.
Figure 12C:
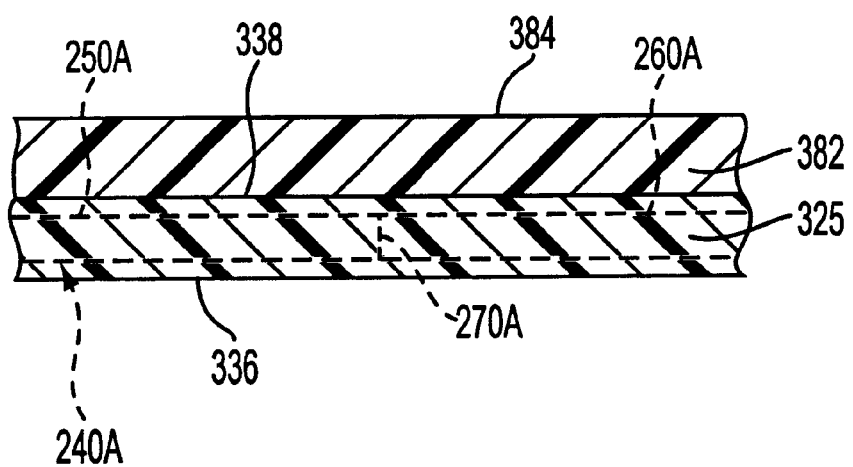
FIG. 12C is a side cross-sectional view of another embodiment of the brain cooling apparatus of FIG. 11.

Alternatively, a chemical pack 260A, such as that shown in FIG. 10, can be disposed within cavity 325, as shown in FIG. 12C, which activates when the membrane 270A between two separate chemical compartments 250A, 260A is broken to mix the two chemicals, providing instant cooling. In such a case, the helmet can be configured to be reusable so that the chemical packet 240A can be replaced.

An inflatable bladder 382 is positioned along the exterior face of the outer shell 338. The bladder 382 upon inflation and subsequent filling with gas (e.g. air) from a gas source 380, the gas supplied through lines 381, 381, press the inner and outer shells 336, 338 (now cooled) against the head 342. This contact permits a greater heat transfer between the brain cooling apparatus and the head 342 and therefore more rapid body cooling.

The inner and outer shells 336 and 338 are joined with outer bladder layer 384 at their peripheral edges (not shown) to form an airtight seal by any one of several conventional bonding constructions such as ultrasonic welding, vibration welding, radio frequency welding, heat welding, electromagnetic welding, and induction welding, as well as thermal sealing and adhesive bonding techniques. The preferred method of joining the inner and outer shells 336, 338 and the outer bladder layer 384 is heat sealing.

Figure 13:
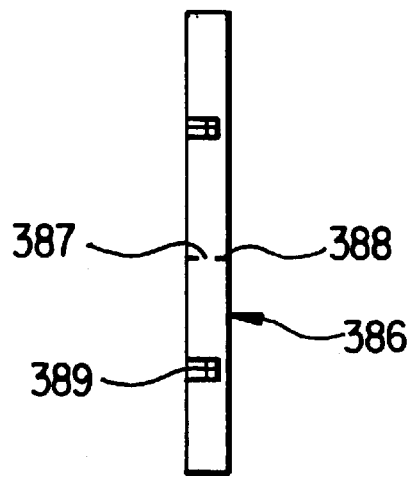
FIG. 13 is a side cross-sectional view of the chambers in the brain cooling apparatus of FIG. 11.
Figure 14:
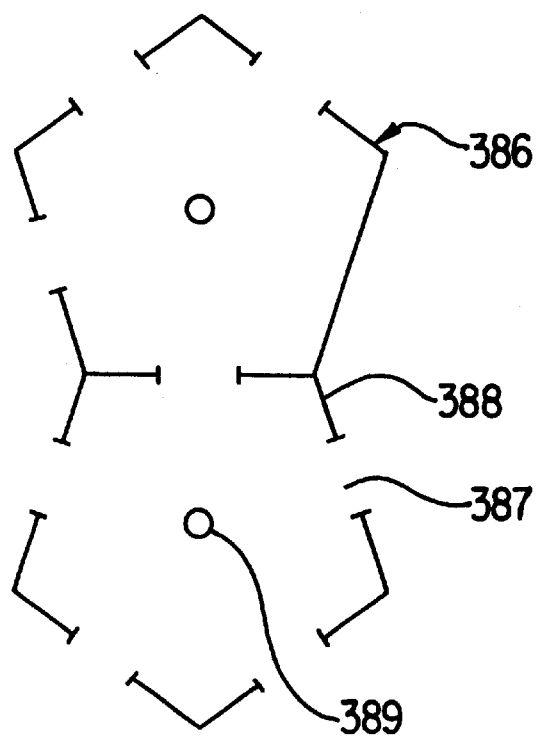
FIG. 14 is a top cross-sectional view of the chambers in the brain cooling apparatus of FIG. 11.

Coolant channels 386, shown in detail in FIGS. 13 and 14, are formed between inner and outer shells 336, 338 and are preferably pentagonal in shape, although other shapes (e.g. hexagonal, triangular, circular, elliptical) are also permissible. The channels 386 include opening 387 in their walls 388, and protrusions 389 at their center. These structures provide turbulent flow for the coolant for effectively cooling. Alternatively, the coolant channels 386 may include the protrusions alone absent the walls.

Alternatively, as shown in FIGS. 12A and 12B, the spaces between the inner and outer shells 336, 338, and/or between the outer shell 338 and the outer bladder layer 384 can define lumens 385 for coolant circulation systems, or gas circulation systems, respectively. The coolant circulation systems, or gas circulation systems would include linear joints (not shown), preferably of a length in the range of approximately 0.2 cm to 10.0 cm, formed by heat sealing portions between the inner and outer shells 336, 338, and/or between the outer shell 338 and the outer bladder layer 384. These linear joints, which may be uniform in size and may be formed in various patterns, such as in a series of side-by-side, parallel rows, or staggered in diagonal or lightening bolts patterns, create a pathway for coolant fluid, or gas to circulate. Such an arrangement permits high fluid flow rates while preventing ballooning, which reduces skin contact, of the apparatus layers.

Tubes (not shown) also may be employed, in a serpentine or similar pattern to maximize cooled surface area, located between the inner and outer shells 336, 338. The tubes may have cross-sectional shapes that are circular, rectangular, square, oval, triangular, diamond, or any other shape suitable to accommodate coolant flow through the tube. The tube or tubes may be attached to either the inner shell 336, the outer shell 338, both or not attached to either.

A preferred coolant source 364 is a refrigeration unit capable of generating cooled fluid (liquid and/or gas) at temperatures as low as −60 degrees Fahrenheit and at pressures as great as 60 psig, and preferably at temperatures approximately—10 degrees Fahrenheit or below and pressures approximately 10 psig or above. Multiple coolant sources are also permissible. Coolant fluid may be any fluid, liquid or gaseous, including chilled water and slushed ice, capable of imparting the desired cooling effect.

Additives may be included to lower the freezing point of the coolant fluid, such as propylene glycol. Propylene glycol exhibits low corrosiveness and low volatility. A bacteriostatic agent may also be added to prevent the growth of bacteria and other organisms.

Additional coolant fluids include R-134A (Forane, 1,1,1, 2-tetrafluoroethane), which is considered to be one of the most environmentally safe refrigerants available. R-134A is nonflammable, does not contain known reproductive toxins, is insoluble in water, has a freezing point below (−)101° C., and is generally stable at low temperatures. Furthermore, R-134A is non-irritating upon contact with the skin, other than by potential excessive cooling. R-134A does not contain components listed by NTP, IARC, or OSHA as being carcinogens. R-134A has a low acute inhalation toxicity (4 hour CCSO in the rat >500,000 ppm).

The coolant inflow and outflow lines 364, 364 supply coolant fluid from and return the coolant fluid to the coolant source as part of a coolant circuit. These coolant inflow and outflow lines 364, 364 are preferably directly connected to the coolant source and the outer shell 338, as shown in FIG. 11, via airtight ports (not shown). Alternatively, the coolant outflow line need not be connected back to the coolant source if a coolant circuit is not desired. Multiple coolant inflow and outflow lines (not shown) are also permissible with this apparatus. The multiple inflow and outflow lines may be directly connected to the coolant source or may be branched and connected to main coolant inflow and outflow lines. Further, the coolant inflow and outflow lines 364, 364, supplying the brain cooling apparatus 330 could include valves anywhere along their length. These valves may be controlled manually, pneumatically, hydraulically, magnetically, or electronically. Thermistor temperature sensors and microprocessors may be used to control the brain cooling apparatus and allow zone cooling, or to enhance coolant control.

As previously described, the outer bladder layer 384 defines the inflatable bladder 382 or alternatively multiple bladders (if partitioned accordingly) that is designed to be inflated with liquid, or gases, to press the inner and outer shells 336, 338 into contact with the head 342. Alternatively, the bladder(s) may be attached to the outer shell 338. The bladder(s) may be inflated with gas from a source 380, the source 380 including pressurized air tanks, portable or solid state air compressors, manually or automatically driven air pumps, or vapor generating chemical reactions. The gas used to inflate the bladder(s) may include any suitable non-toxic gas, including air, nitrogen, helium, oxygen, and carbon dioxide.

Alternatively, the gas source may include several valves for attaching to multiple gas lines. Each valve may be under microprocessor control or each valve may be part of a series of automatically cycling valves. This allows each valve to control the supply of inflation gas to a single bladder (in multiple bladder devices) to create wave-like inflation of the bladders.

Another alternative gas supply may provide gas in repeating inflation and deflation modes, in response to preset or regulated pressures, or time, or flow. The gas source would include a supply of any of the inflation gases disclosed above, and would also include specialized pumps, pressure sensors and valves, electronically connected, and preferably under microprocessor control (with a manual override) that serve to inflate the bladder(s) and then deflate them when a preset pressure is reached. Once deflation reaches a preset pressure, the bladder(s) is/are inflated. This can continue for as long as desired, as is controlled by the user.

The bladder 382 is connected and supplied inflation gas thereto, from the gas source 380 by lines 381, 381 or multiple lines (not shown) from the gas source 380. Multiple gas sources are also permissible. The lines 381, 381 may be permanently attached but are preferably removably connected. The lines 381, 381 connect to the outer bladder layer 384 via airtight ports (not shown). The ports preferably include valves (not shown), such as a check valve or stop cock to prevent escape of gas from the bladder 382, once the lines 381, 381 are disconnected, or to permit the input or discharge of gas as desired. The ports may be located anywhere along the outer bladder layer 382.

The inner and outer shells 336, 338 and the outer bladder layer 384 are preferably made of a material impervious to liquid and gas. Thermoplastic elastomers (TPEs) which can be made into film or sheeting by extrusion casting, calendering, or other manufacturing processes are appropriate. Included among these TPEs are polyurethane, copolyesters, styrene copolymers, olefins, and elastomeric alloys. Preferred TPEs will have good elongation and tear strength, good resistance to flex fatigue at both low and high temperatures, good dynamic properties, resist water, alcohols, and dilute bases and acids, and exhibit good thermal conduction properties to permit the rapid transfer of heat from the person or cadaver. The materials for the inner and outer shells may also comprise TEFLON® TYVEK® or Gore-tex® type materials or the like.

The material of the inner shell may include microscopic pores. These microscopic pores permit small quantities of coolant to enter the cavity (on the side of the inner layer contacting the body) and moisten the skin. This skin moistening destroys the insulative air layer that exists on the skin and allows direct contact with the cooled inner layer for maximum heat transfer to the head.

The inner shell may also be coated with gel, with gels such as any commercially available EKG electrode gel or ultrasound gel. The gel could be retained under paper, wax-based or TYVEK® type sheets, that peel off when use of the apparatus is desired.

The material for the outer bladder layer may also comprise TEFLON®, TYVEC® Gore-tex®, nylon, rubber or any non-porous flexible material.

Figure 15:
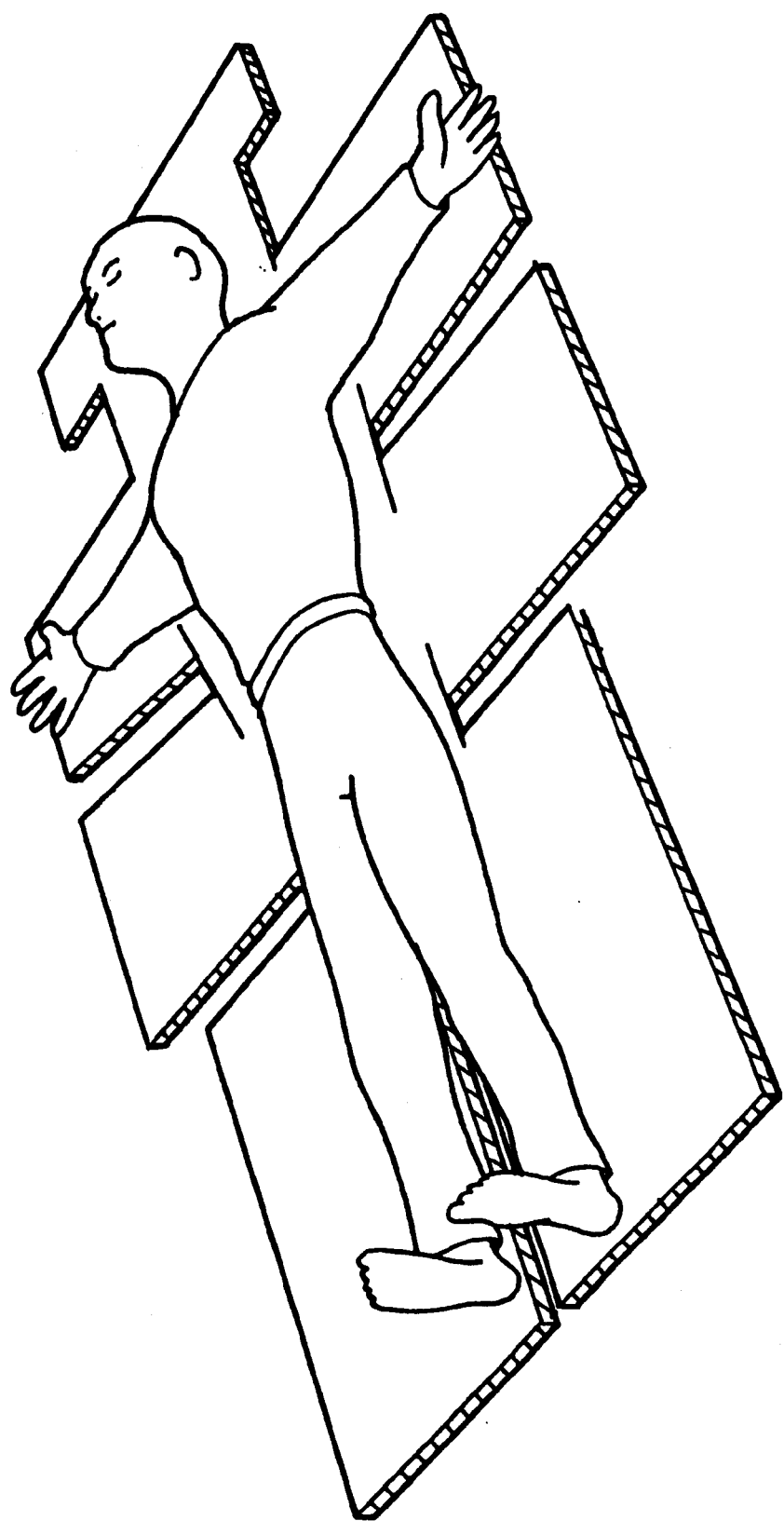
FIG. 15 shows the brain cooling apparatus of FIG. 11 extended to provide total body cooling.

Alternatively, the outer bladder layer may be eliminated and the inner and outer shells may be pressed against the head by a formfitting stretchable cap that fits snugly on the head. Also, the inner and outer shells may extend down around the eyes to provide cooling to the eyes. Further, the gas source may be replaced by a vacuum source for creating a vacuum in the cavity formed between the head of a patient and the inner shell. Also, the brain cooling device can extend down the back, e.g., to provide total body cooling, preferably in sections, as shown, by example, in FIG. 15.

Similar to the other embodiments, operation of the apparatus involves merely placing and securing the brain cooling apparatus on the patient's head; attaching the coolant inflow and outflow lines to the outer shell and the coolant source(s); attaching the gas inflow and outflow lines to the outer bladder layer and the gas source(s); and activating the coolant source(s) and the gas source(s). This process is quite simple and can be performed at the trauma site by a person with minimal, if any, medical training.

These embodiments of the apparatus are portable and suitable for field use, such as in ambulances, battlefields, athletic fields, aircraft, marine vehicles, spacecraft, emergency treatment facilities, and the like. They are lightweight and can be carried directly to the patient. These embodiments can also be modified for clinical (hospital type) settings. While the apparatus of the present invention is preferably designed for the treatment of humans, it can also be used in treating other mammals such as dogs, horses or the like, and sized accordingly.

While particular embodiments of the invention have been shown, it will be understood, of course, that the invention is not limited thereto, since modifications may be made by those skilled in the art, particularly in light of the foregoing teachings. It is therefore, contemplated by the appended claims to cover any such modifications as incorporate those features which constitute the essential features within the true spirit and scope of the invention.

What is claimed is:

1. A portable apparatus for treating or preventing at least one of brain, brain-stem and associated nervous tissue injuries in a mammal suffering from decreased or compromised blood flow to the brain, comprising:

enveloping means for enveloping a head of a mammal, the enveloping means comprising a helmet configured to rest unsupported on the head of a mammal, the helmet including outer and inner shells with at least one cavity intermediate the outer and inner shells for holding a coolant fluid within the at least one cavity;

a manually activated and controlled coolant source in communication with the enveloping means, the coolant source instantaneously providing a coolant fluid chilled to a temperature sufficient to slow the metabolism of the brain, whereby when the coolant source is activated, the enveloping means becomes instantly chilled rapidly cooling the brain to a temperature sufficient to slow the metabolism of the brain a sufficient amount so that the mammal remains neurologically intact while efforts are made to restore regular blood flow to the brain of the mammal; and pressing means for pressing a radially inward surface of the enveloping means against the head of a mammal.

2. The apparatus according to claim 1, wherein the coolant source is disposed within the at least one cavity and comprises a packet containing chemicals which are activated upon mixing to produce the chilled coolant fluid.

3. The apparatus according to claim 1, wherein the coolant source comprises a charging mechanism disposed on an outer surface of the outer shell which upon activation produces the chilled coolant fluid.

4. The apparatus according to claim 1, wherein the coolant source comprises a portable coolant tank containing compressed liquid, the portable coolant tank being in fluid communication with the at least one cavity of the enveloping means via a tube.

5. The apparatus according to claim 4, wherein the compressed liquid is selected from the group consisting of carbon dioxide, freon and nitrogen.

6. The apparatus according to claim 1, wherein the coolant source comprises a chemical disposed within the at least one cavity which produces the chilled coolant fluid when activated by another chemical.

7. The apparatus according to claim 6, wherein the chemical comprises ammonium nitrate which produces the chilled coolant fluid when activated by water.

8. The apparatus according to claim 1, wherein the inner and outer shells are formed of a soft, flexible material.

9. The apparatus according to claim 1, further comprising padding disposed on a surface of the inner shell, the padding being of a material which allows the chill to quickly reach the brain.

10. The apparatus according to claim 1, wherein the enveloping means is configured to be disposable.

11. The apparatus according to claim 1, further comprising flexible adjusting means for maintaining the enveloping means on the head of a mammal.

12. The apparatus according to claim 1, wherein the pressing means comprises at least one inflatable bladder, an inflation device in communication with the at least one inflatable bladder, wherein the at least one inflatable bladder is inflated by the inflation device to press the radially inward surface of the enveloping means against the head of a mammal.

13. The apparatus according to claim 1, wherein the enveloping means further comprises at least one coolant distribution system within the enveloping means; and wherein the pressing means comprises at least one inflatable bladder, an inflation device in communication with the at least one inflatable bladder, wherein the at least one inflatable bladder is inflated by the inflation device to press the at least one coolant distribution system against the head of a mammal.

14. The apparatus according to claim 1, wherein the enveloping means further comprises at least one coolant distribution system formed by and between the inner and outer shells, wherein the pressing means comprises at least one inflatable bladder disposed on the outer shell of the enveloping means, the at least one inflatable bladder being in communication with an inflation device, and wherein the at least one inflatable bladder is inflated by the inflation device to press the at least one coolant distribution system against the head of a mammal to effectuate cooling of the head of the mammal.

15. The apparatus according to claim 1, further comprising at least one temperature sensor for sensing a temperature of the chilled coolant fluid within the helmet.

16. The apparatus according to claim 15, wherein the at least one temperature sensor comprises a thermistor.

17. The apparatus according to claim 14, further comprising a layer of gel disposed on an inner surface of the inner shell.

18. The apparatus according to claim 1, wherein portions of the enveloping means extend to cover the forehead and cheeks of the head of a mammal.

19. The apparatus according to claim 1, wherein the enveloping means further comprises a portion that extends to cover the eyes of a mammal.

20. A method for treating or preventing at least one of brain, brain stem and associated nervous tissue injuries in a mammal suffering from decreased or compromised blood flow to the brain, comprising:

placing on a head of a mammal an enveloping means, the enveloping means comprising a helmet configured to rest unsupported on the head of a mammal, the helmet including outer and inner shells with at least one cavity intermediate the outer and inner shells for holding a coolant fluid within the at least one cavity;

lowering the metabolism of the brain of the mammal by activating a manually activated and controlled coolant source in communication with the enveloping means, the coolant source providing a coolant fluid instantaneously chilled upon activation to a temperature sufficient to slow the metabolism of the brain of the mammal a sufficient amount so that the mammal remains neurologically intact while efforts are made to restore regular blood flow to the brain of the mammal; and pressing a radially inward surface of the enveloping means against the head of a mammal with an inflatable bladder.

21. The method of claim 20, wherein the coolant source is disposed within the at least one cavity and comprises a packet containing chemicals which are activated upon mixing to produce the chilled coolant fluid.

22. The method of claim 20, wherein the coolant source comprises a charging mechanism disposed on an outer surface of the outer shell.

23. The method of claim 20, wherein the coolant source comprises a portable coolant tank containing a compressed liquid, the portable coolant tank being in fluid communication with the at least one cavity of the enveloping means via a tube.

24. The method according to claim 20, wherein the coolant source comprises a chemical disposed within the at least one cavity which produces the chilled coolant fluid when activated by another chemical.

25. The method according to claim 24, wherein the chemical comprises ammonium nitrate which produces the chilled coolant fluid when activated by water.

26. The method according to claim 20, wherein the inner and outer shells are formed of a soft, flexible material.

27. The method according to claim 20, wherein the enveloping means is configured to be disposable.

28. A method for treating or preventing at least one of brain, brain stem and associated nervous tissue injuries in a mammal suffering from decreased or compromised blood flow to the brain, comprising:

placing on a head of a mammal an enveloping means, the enveloping means comprising a helmet configured to rest unsupported on the head of a mammal, the helmet including outer and inner shells with at least one cavity intermediate the outer and inner shells for holding a coolant fluid within the at least one cavity;

lowering the metabolism of the brain of the mammal by activating an instantaneously activatable coolant source disposed at least one of on an outer surface of the outer shell of the helmet and within the at least one cavity and in communication with the enveloping means, the coolant source providing a coolant fluid instantaneously chilled upon activation to a temperature sufficient to slow the metabolism of the brain of the mammal a sufficient amount so that the mammal remains neurologically intact while efforts are made to restore regular blood flow to the brain of the mammal; and pressing a radially inward surface of the enveloping means against the head of a mammal with an inflatable bladder.

29. The method of claim 28, wherein the coolant source is disposed within the at least one cavity and comprises a packet containing chemicals which are activated upon mixing to produce the chilled coolant fluid.

30. The method of claim 28, wherein the coolant source comprises a charging mechanism disposed on an outer surface of the outer shell.

31. The method of claim 28, wherein the coolant source comprises a portable coolant tank containing a compressed liquid, the portable coolant tank being in fluid communication with the at least one cavity of the enveloping means via a tube.

32. The method according to claim 28, wherein the coolant source comprises a chemical disposed within the at least one cavity which produces the chilled coolant fluid when activated by another chemical.

33. The method according to claim 32, wherein the chemical comprises ammonium nitrate which produces the chilled coolant fluid when activated by water.

34. The method according to claim 28, wherein the inner and outer shells are formed of a soft, flexible material.

35. The method according to claim 28, wherein the enveloping means is configured to be disposable.

36. A portable apparatus for treating or preventing at least one of brain, brain-stem and associated nervous tissue injuries in a mammal suffering from decreased or compromised blood flow to the brain, comprising:

a helmet configured to rest unsupported on the head of a mammal, the helmet including outer and inner shells with at least one cavity intermediate the outer and inner shells for holding a coolant fluid within the at least one cavity;

a manually activated and controlled coolant source in communication with the helmet, the coolant source instantaneously providing a coolant fluid chilled to a temperature sufficient to slow the metabolism of the brain, whereby when the coolant source is activated, the helmet becomes instantly chilled rapidly cooling the brain to a temperature sufficient to slow the metabolism of the brain a sufficient amount so that the mammal remains neurologically intact while efforts are made to restore regular blood flow to the brain of the mammal; and an inflatable bladder that presses a radially inward surface of the helmet against the head of a mammal when inflated.

37. A portable apparatus for treating or preventing at least one of brain, brain-stem and associated nervous tissue injuries in a mammal suffering from decreased or compromised blood flow to the brain, comprising:

a helmet configured to rest unsupported on the head of a mammal, the helmet including outer and inner shells with at least one cavity intermediate the outer and inner shells for holding a coolant fluid within the at least one cavity; an instantaneously activatable coolant source in communication with the helmet, the coolant source being disposed at least one of on the outer shell of the helmet and within the at least one cavity and providing a coolant fluid chilled to a temperature sufficient to slow the metabolism of the brain, whereby when the coolant source is activated, the helmet becomes instantly chilled rapidly cooling the brain to a temperature sufficient to slow the metabolism of the brain a sufficient amount so that the mammal remains neurologically intact while efforts are made to restore regular blood flow to the brain of the mammal; and an inflatable bladder that presses a radially inward surface of the helmet against the head of a mammal when inflated.

* * * * *